(12) United States Patent
Soppet et al.

(10) Patent No.: US 6,372,891 B1
(45) Date of Patent: Apr. 16, 2002

(54) HUMAN G-PROTEIN RECEPTOR HPRAJ70

(75) Inventors: Daniel R. Soppet, Centreville, VA (US); Yi Li, Gaithersburg, MD (US); Craig A. Rosen, Laytonsville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/339,115

(22) Filed: Jun. 24, 1999

Related U.S. Application Data

(62) Division of application No. 09/053,303, filed on Apr. 1, 1998, now Pat. No. 5,948,890, which is a division of application No. 08/465,980, filed on Jun. 6, 1995, now Pat. No. 5,756,309.

(51) Int. Cl.[7] ............................................. C07K 16/28
(52) U.S. Cl. ................. 530/387.9; 530/388.1; 530/388.22; 530/387.1; 530/387.3; 530/389.1; 530/350
(58) Field of Search .......................... 530/387.9, 388.1, 530/388.22, 387.1, 387.3, 389.1, 350

(56) References Cited

FOREIGN PATENT DOCUMENTS

WO   WO 92/17585   10/1992

OTHER PUBLICATIONS

Bowie et al. Science 247:1306–1310), 1990.*
Skolnick et al., Trends in Biotech 18(1): 34–39, Jan. 2000.*
Lee, N. H. et al., Drugs & Perspectives, vol. 6(7):488–497 (1993).
Oliveira L. et al., J. Computer–Aided Molecular Design, vol. 7(6):649–658 (1993).
European Search Report (EP 95 92 1605) (1999).
Ross P.C. et al., Proc. Natl. Acad. Sci., vol. 87:3052–3056 (1990).
Libert F. et al., Science, vol. 244:568–572(1989).
Eva C., et al., FEBS Letter, vol. 271:81–84 (1990).
Buck and Axel, Cell 65(1): 175–187 (1991).
Hla et al., The Journal of Biological Chemistry 265(16): 9308–9316 (1990).
Linda L. Zu, et al., "PSGR, a Novel Prostate–specific Gene with Homology to a G Protein–coupled Receptor, Is Overexpressed in Prostate Cancer," *Cancer Research,* 60: 6568–6572 (2000).
Shelagh Wilson, et al., "Orphan G–protein–coupled receptors: the next generation of drug targets?", *British Journal of Pharmacology* 125: 1387–1392 (1998).
Julie A. Pitcher, et al., "G Protein—Coupled Receptor Kinases," *Annu. Rev. Biochem.* 67: 653–92 (1998).
Jeffrey M. Stadel, et al., "Orphan G protein–coupled receptors: a neglected opportunity for pioneer drug discovery," *TiPS* 18: 430–437 (1997).
Stephen W. Edwards, et al., "Localization of G–protein–coupled receptors in health and disease," *TiPS* 21: 304–308 (2000).
Rennolds S. Ostrom, et al., "Stoichiometry and Compartmentation in G Protein–Coupled Receptor Signaling: Implications for Therapeutic Interventions Involving $G_{s1}$", *The Journal of Pharmacology and Experimental Therapeutics* 294 (2): 407–412 (2000).

* cited by examiner

Primary Examiner—Gary L. Kunz
Assistant Examiner—Eliane Lazar-Wesley
(74) *Attorney, Agent, or Firm*—Human Genome Sciences, Inc.

(57) ABSTRACT

Human G-protein coupled receptor polypeptides and DNA (RNA) encoding such polypeptides and a procedure for producing such polypeptides by recombinant techniques is disclosed. Also disclosed were methods for utilizing such polypeptides for identifying antagonists and agonists to such polypeptides and methods of using the agonists and antagonists therapeutically to treat conditions related to the underexpression and overexpression of the G-protein coupled receptor polypeptides. Also disclosed are diagnostic methods for detecting a mutation, in the G-protein coupled receptor nucleic acid sequences and an altered level of the soluble form of the receptors.

32 Claims, 9 Drawing Sheets

FIG. 1A

```
                    10                  30                    50
  1    CCATGCTGCCTTCCGGGCAGTACCATCCATTCCACACCCTGGAAGACACAGTGAGTTAG     60
                    70                  90                    110
 61    CACCACCACCAGGTAATTGGCCTTATCAGTCTCTGTGCCTGTCTCCAGTCAGGCTGGAATA  120
                   130                 150                    170
121    AGTCTCCTCATATGTGCAAGCTCGGCCCTCCCCCTGGAATCTAAAGCCTCCTCAGCCTTCT  180
                   190                 210                    230
181    GAGTCAGCCTGAAAGGAACAGGCCGAACTGCTGTATGGGCTTACTGCCAGTGTGACCTC    240
                   250                 270                    290
241    ACCCTCTCCAGTCACCCCTCCTCAGTTCCAGTATGAGTTCCTGCAACTTCACACATGCC    300
  1                                              M  S  S  C  N  F  T  H  A     9
                   310                 330                    350
301    ACCTGTGTGCTTATTGGTATCCCAGGATTAGAGAAAGCCCATTTCTGGGTTGGCTTCCCC   360
 10     T  C  V  L  I  G  I  P  G  L  E  K  A  H  F  W  V  G  F  P        29
                   370                 390                    410
361    CTCCTTTCCATGTATGTAGTGGCAATGTGTGGAAACTGCATCGTGGTCTTCATCGTAAGG   420
 30     L  L  S  M  Y  V  V  A  M  C  G  N  C  I  V  V  F  I  V  R        49
```

FIG. 1B

```
           430                450                470
421  ACGGAACGCAGCCTGCACGCTCCGATGTACCTCTTTCTGCATGCTTGCAGCCATTGAC  480
 50   T  E  R  S  L  H  A  P  M  Y  L  F  L  C  M  L  A  A  I  D   69

490                510                530
481  CTGGCCTTATCCACATCCACCATGCCTAAGATCCTTGCCCTTTTCTGGTTTGATTCCGA  540
 70   L  A  L  S  T  S  T  M  P  K  I  L  A  L  F  W  F  D  S  R   89

550                570                590
541  GAGATTAGCATTGAGGCCTGTCTTACCCAGATGTTCTTATTCATGCCCTCTCAGCCATT  600
 90   E  I  S  I  E  A  C  L  T  Q  M  F  F  I  H  A  L  S  A  I  109

610                630                650
601  GAATCCACCATCCTGTGGCCATGGCCTTTGACCGTTATGTGGCCATCTGCCACCCACTG  660
110   E  S  T  I  L  L  A  M  A  F  D  R  Y  V  A  I  C  H  P  L  129

670                690                710
661  CGCCATGCTGCAGTGCTCAACAATACAGTAACAGCCCAGATTGGCATCGTGGCTGTGGTC  720
130   R  H  A  A  V  L  N  N  T  V  T  A  Q  I  G  I  V  A  V  V  149

730                750                770
721  CGCGGATCCCTCTTTTTCCCACTGCCTCTGTGATCAAGCGGCTTGCCTTCTGCCAC  780
150   R  G  S  L  F  F  F  P  L  P  L  L  I  K  R  L  A  F  C  H  169
```

FIG. 1C

```
        790                800                810                820                830                840
781 TCCAATGTCCTCTCGCACTCCTATTGTCCACCAGGATGTAATGAAGTTGGCCTATGCA  840
170   S  N  V  L  S  H  S  Y  C  V  H  Q  D  V  M  K  L  A  Y  A   189

850                860                870                880                890                900
841 GACACTTTGCCCAATGTGGTATATGGTCTTACTGCCATTCTGCTGGTCATGGGCGTGGAC  900
190   D  T  L  P  N  V  V  Y  G  L  T  A  I  L  L  V  M  G  V  D   209

910                920                930                940                950                960
901 GTAATGTTCATCTCCCTTGTCCTATTTCTGATAATACGAACGGTTCTGCAACTGCCTTCC  960
210   V  M  F  I  S  L  S  Y  F  L  I  R  T  V  L  Q  L  P  S      229

970                980                990               1000               1010               1020
961 AAGTCAGAGCGGGCCAAGGCCTTTGGAACCTGTGTCACACATTGGTGTGGTACTCGCC  1020
230   K  S  E  R  A  K  A  F  G  T  C  V  S  H  I  G  V  V  L  A   249

1030               1040               1050               1060               1070               1080
1021 TTCTATGTGCCACTTATTGGCCCTCTCAGTTGTACACCGCTTGGAAACAGCCTTCATCCC  1080
250   F  Y  V  P  L  I  G  L  S  V  V  H  R  F  G  N  S  L  H  P   269

1090               1100               1110               1120               1130               1140
1081 ATTGTGCGTGTTGTCATGGGTGACATCTACCTGCTCCTGCCTCCTGTCATCAATCCCATC  1140
270   I  V  R  V  V  M  G  D  I  Y  L  L  L  P  P  V  I  N  P  I   289
```

FIG. 1D

```
                              1150                            1170                            1190
1141   ATCTATGGTGCCAAAACCAAACAGATCAGAACACGGGTGCTGGCTATGTTCAAGATCAGC   1200
290     I  Y  G  A  K  T  K  Q  I  R  T  R  V  L  A  M  F  K  I  S      309

1210                            1230                            1250
1201   TGTGACAAGGACTTGCAGGCTGTGGGGAGGCAAGTGACCCCTTAACACTACACTTCTCCTTA   1260
310     C  D  K  D  L  Q  A  V  G  G  K  *                              320

1270                            1290                            1310
1261   TCTTTATTGGCTTGATAAACATAATTATTCTAACACTAGCTATTCCAGTTGCCCATA    1320

1330                            1350                            1370
1321   AGCACACATCAGTACTTTCTCTGGCTGGAATAAAGTATGGTACATCTACCTAA        1380

1390                            1410                            1430
1381   AGGACTATTATGTGGAATAATACATACTAATGAAGTATTACATGATTTAAAGACTACAAT 1440

1450                            1470
1441   AAAACCAAACATGCTTATAACATTAAAAAAAAA    1474
```

FIG. 3A

Sequences producing High-scoring Segment Pairs:

```
                                                              High     Probability
                                                              Score    P/(N)       N
gi|320861gp|X64994|HSHGM071_1 HGMP071 gene product [Homo ...  402      6.6e-53     1
gi|205844|gp|M64391|RATOLFPROQ_1 olfactory protein [Rattu...  402      6.7e-53     1
pir|S29708 olfactory receptor OR12 - rat                      399      2.4e-52     1
pir|A60547 hypothetical protein (HPFH breakpoint 3' reg...    394      1.9e-51     1
gi|205846|gp|M64392|RATOLFPROR_1 olfactory protein [Rattu...  392      3.3e-50     1
pir|S29707 olfactory receptor OR5 - rat                       389      1.3e-49     1
pir|S29711 olfactory factor OR37 - rat                        386      1.6e-49     1
gi|205832|gp|M64385|RATOLFPROK_1 olfactory protein [Rattu...  382      2.0e-48     1
gi|425222|gp|X65857|HSHGM07EG_1 G protein-coupled recepto...  381      3.5e-48     1
gi|205816|gp|M64377|RATOLFPROC_1 olfactory protein [Rattu...  376      2.8e-47     1
```

WARNING:  Descriptions of 494 database sequences were not reported due to the limiting value of parameter V = 10.

>gi|320861gp|X64994|HSHGM071_1 HGMP071 gene product [Homo sapiens]
    >pir|S20572 olfactory receptor - human >sp|P30953|OLFI_HUMAN
    OLFACTORY RECEPTOR-LIKE PROTEIN HGMP071.
    Length = 314

Score = 402 (191.1 bits), Expect = 6.6e-53, P = 6.6e-53
Identities = 88/247 (35%), Positives = 138/247 (55%)

FIG. 3B

```
Query:  11  FVLIGIPGLEKAHFWVGFPLLSMYVVAMCGNCIVVFIVRTERSLHAPMYLFLCMLAAIDL  70
            F+L+G+P    +           L+MY+ + GN +++ ++R +  LH PMYLFL  L+ DL
Sbjct:  12  FLLLGLPIQPEQQNLCYALFLAMYLTTLLGNLLIIVLIRLDSHLHTPMYLFLSNLSFSDL  71

Query:  71  ALSTSTMPKILALFWFDSREISFEACLTQMFFIHALSAIESTILLAMAFDRYVAICHPLR  130
            +          S+ T+PK+L       I + CLTQM+F                 +ES +L+AMA+DRYVAIC PL
Sbjct:  72  CFSSVTIPKLLQNMQNQDPSIPYADCLTQMYFFLLFGDLESFLLVAMAYDRYVAICFPLH  131

Query:  131 HAAVLNNTVTAQIGIVAVVRGSLFFFPLPLLIKRLAFCHSNVLSHSYCVHQDVMKLAYAD  190
            +    A+++ +  +  ++V +         LL+ RL FC NV+ H +C    ++KLA++D
Sbjct:  132 YTAIMSPMLCLALVALSWVLTTFHAMLHTLLMARLCFCADNVIPHFFCDMSALLKLAFSD  191

Query:  191 TLPNVVYGLTAILLVMGVDVMFISLSYFLIIRTVLQLPSKSERAKAFGTCVSHIGVVLAF  250
                 T    N         L++   +   I  SY  I+  +     +L++PS      KAF TC SH+ VV  F
Sbjct:  192 TRVNEWVIFIMGGLILVIPFLLILGSYARIVSSILKVPSSKGICKAFSTCGSHLSVVSLF  251

Query:  251 YVPLIGL  257
            Y  +IGL
Sbjct:  252 YGTVIGL  258
```

FIG. 3C

```
Score = 54 (25.7 bits), Expect = 0.0049, Poisson P(2) = 0.0049
Identities = 8/26 (30%), Positives = 17/26 (65%)

Query:   274 VMGDIYLLLPPVINPIIYGAKTKQIR 299
             VM +Y ++ P++NP IY + + ++
Sbjct:   273 VMAMMYTVVTPMLNPFIYSLRNRDMK 298

>gi|205844|gp|M64391|RATOLFPROO_1 olfactory protein [Rattus norvegicus]
             >pir|S|I23701 olfactory receptor I14 - rat >sp|P23273|OLF4_RAT
             OLFACTORY RECEPTOR-LIKE PROTEIN I14.
          Length = 312

Score = 402 (191.1 bits), Expect = 6.7e-53, P = 6.7e-53
Identities = 88/256 (34%), Positives = 139/256 (54%)

Query:    11 FVLIGIPGLEKAHFWVGFPLLSMYVVAMCGNCIVVFIVRTERSLHAPMYLFLCMLAAIDL 70
             F+L+G+P    + H     L+MY+   + GN +++ +VR + LH PMYLFL L+ DL
```

HUMAN G-PROTEIN RECEPTOR HPRAJ70

This application is a Divisional of U.S. patent application Ser. No. 09/053,303, filed Apr. 1, 1998, now U.S. Pat. No. 5,948,890, which is a Divisional of U.S. patent application Ser. No. 08/465,980 filed Jun. 6, 1995, now U.S. Pat. No. 5,756,309, all of which are incorporated herein by reference in their entireties.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as a prostate tissue receptor, sometimes hereinafter referred to as "HPRAJ70". The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka et al., PNAS, 84:46–50 (1987); Kobilka et al., Science, 238:650–656 (1987); Bunzow et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

In accordance with one aspect of the present invention, there are provided novel polypeptides as well as biologically active and diagnostically or therapeutically useful fragments and derivatives thereof. The polypeptides of the present invention are of human origin.

In accordance with another aspect of the present invention, there are provided isolated nucleic acid molecules encoding the polypeptide of the present invention including mRNAs, DNAs, cDNAs, genomic DNA as well as antisense analogs thereof and biologically active and diagnostically or therapeutically useful fragments thereof.

In accordance with a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said polypeptide and subsequent recovery of said polypeptide.

In accordance with yet a further aspect of the present invention, there are provided antibodies against such polypeptides.

In accordance with another aspect of the present invention there are provided methods of screening for compounds which bind to and activate or inhibit activation of the receptor polypeptides of the present invention and for receptor ligands.

In accordance with still another embodiment of the present invention there is provided a process of using such activating compounds to stimulate the receptor polypeptide of the present invention for the treatment of conditions related to the under-expression of the G-protein coupled receptors.

In accordance with another aspect of the present invention there is provided a process of using such inhibiting compounds for treating prostatic cancer and other conditions associated with over-expression of the G-Protein receptor polypeptide.

In accordance with yet another aspect of the present invention there is provided non-naturally occurring synthetic, isolated and/or recombinant polypeptides which are fragments, consensus fragments and/or sequences having conservative amino acid substitutions, of at least one transmembrane domain of the G-protein coupled receptor of the present invention, such that the receptor may bind G-protein coupled receptor ligands, or which may also modulate, quantitatively or qualitatively, G-protein coupled receptor ligand binding.

In accordance with still another aspect of the present invention there are provided synthetic or recombinant G-protein coupled receptor polypeptides, conservative substitution and derivatives thereof, antibodies, anti-idiotype antibodies, compositions and methods that can be useful as potential modulators of G-protein coupled receptor function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various G-protein coupled receptors or fragments thereof, as receptor types and subtypes.

In accordance with yet a further aspect of the present invention, there is also provided diagnostic probes comprising nucleic acid molecules of sufficient length to specifically hybridize to the nucleic acid sequences of the present invention.

In accordance with yet another object of the present invention, there is provided a diagnostic assay for detecting a disease or susceptibility to a disease related to a mutation in a nucleic acid sequence of the present invention.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1D shows the cDNA sequence and the corresponding deduced amino acid sequence of the G-protein coupled receptor of the present invention. The standard one-letter abbreviation for amino acids is used.

FIGS. 3A–3C illustrates an amino acid alignment of the G-protein coupled receptor of the present invention and the human HGMPO71 olfactory receptor. Faded areas are those areas which Catch with the other amino acid sequences in the figure.

Figure 2A:
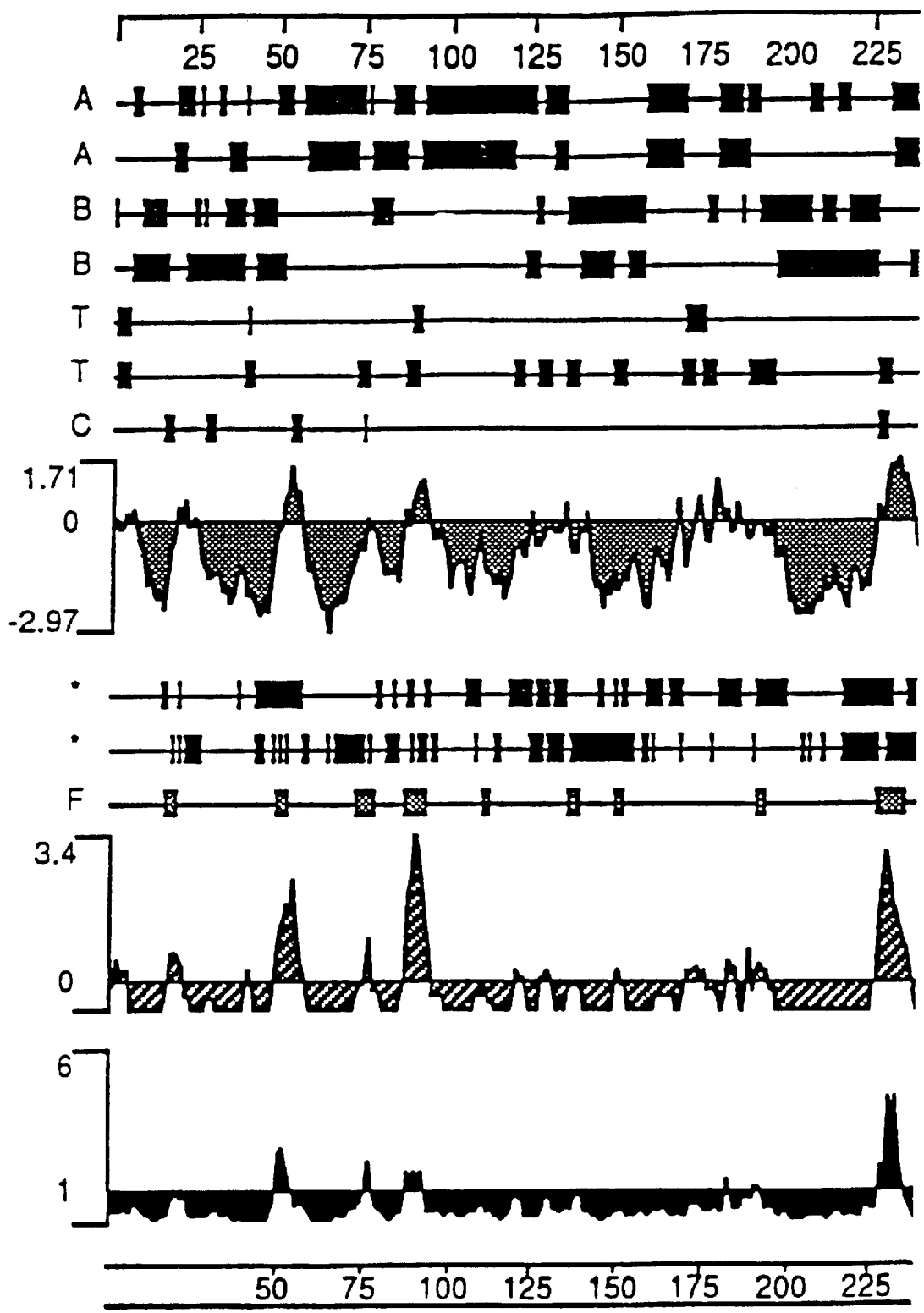
FIGS. 2A and 2B is an illustration of the secondary structural features of the G-protein coupled receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity plot illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antigens. The surface probability plot further corresponds to the antigenic index and the hydrophilicity plot. The amphipathic plots show those regions of the protein sequences which are polar and non-polar. The flexible regions correspond to the second set of illustrations in the sense that flexible regions are those which are outside the membrane and inflexible regions are transmembrane regions.
Figure 2B:
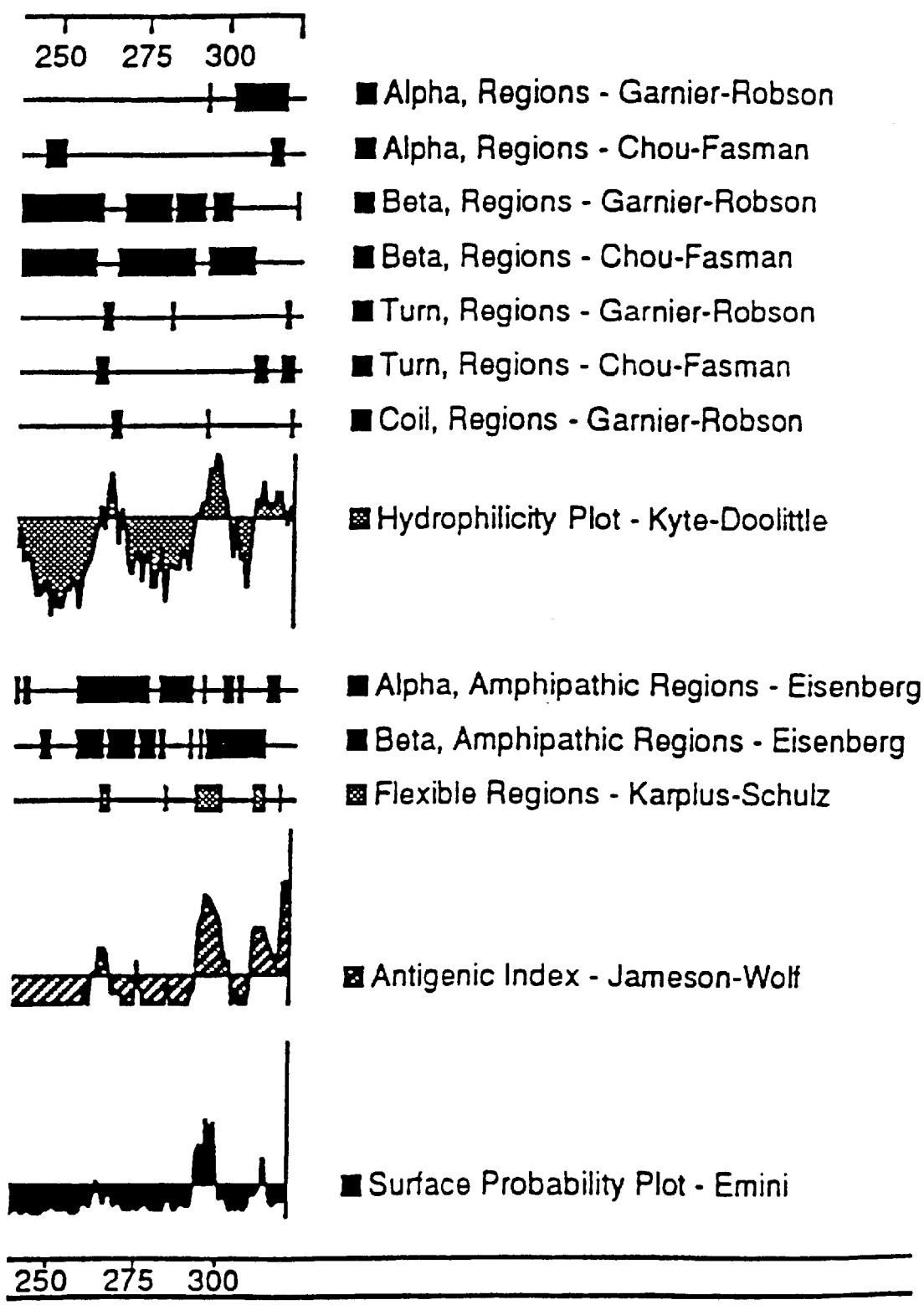

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited with the American Type Culture Collection ("ATCC") on Apr. 28, 1995 and assigned ATCC Deposit No. 97131. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A polynucleotide encoding a polypeptide of the present invention may be found in human prostate. The polynucleotide of this invention was discovered in a cDNA library derived from human prostate tissue. It is structurally related to the G protein-coupled receptor family. It contains an open reading frame encoding a protein of 320 amino acid residues. The protein exhibits the highest degree of homology to the human HGMPO71 olfactory receptor with 33.441% identity-and 58.842% similarity over a 320 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1D (SEQ ID NO:1) or that of the deposited clone or may be a different coding sequence which coding sequence, as a result of the redundancy or degeneracy of the genetic code, encodes the same mature polypeptide as the DNA of FIGS. 1A–1D (SEQ ID NO:1) or the deposited cDNA.

The polynucleotide which encodes for the mature polypeptide of FIGS. 1A–1D (SEQ ID No:2) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1D (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1D (SEQ ID NO:2) or the same mature polypeptide encoded by the cDNA of the deposited clone as well as variants of such polynucleotides which variants encode for a fragment, derivative or analog of the polypeptide of FIGS. 1A–1D (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1D (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the receptor polypeptide of the present invention which is the extracellular portion of the polypeptide which has been cleaved from the TM and intracellular domain of the full-length polypeptide of the present invention.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a portion of the polypeptide from the cell.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson et al., *Cell,* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length HPRAJ70 gene may be used as a hybridization probe for a cDNA library to isolate the full length gene and to isolate other genes which have a high sequence similarity to the gene or similar biological activity. Probes of this type preferably have at least 20 or 30 bases and may contain, for example, 50 or more bases. The probe may also be used-to identify a cDNA clone corresponding to a full length transcript and a genomic clone or clones that contain the complete HPRAJ70 gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1D (SEQ ID NO:1) or the deposited cDNA(s).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity,, preferably at least 90% and more preferably at least a 95% identity to a polynucleotide which encodes the polypeptide of SEQ ID NO:2 as well as fragments thereof, which fragments have at least 30 bases and preferably at least So bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as a convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a G-protein coupled receptor polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIGS. 1A–D (SEQ ID NO:2) or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1D or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the HPRAJ70 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is. operatively linked to an appropriate expression control sequence (s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, *Salmonella typhimurium;* fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3a, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis et al., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters; Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual,* Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3(Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The G-protein coupled receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the G-protein coupled receptor. The expressed receptor is then contacted with a test compound to observe binding, stimulation or inhibition of a functional response.

One such screening procedure involves the use of melanophores which are-transfected to express the G-protein coupled receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

G-protein coupled receptors are ubiquitous in the mammalian host and are responsible for many biological functions, including many pathologies. Accordingly, it is desirous to find compounds and drugs which stimulate the G-protein coupled receptor on the one hand and which can inhibit the function of a G-protein coupled receptor on the other hand.

For example, compounds which activate the G-protein coupled receptor may be employed for therapeutic purposes, such as the treatment of asthma, Parkinson's disease, acute heart failure, hypotension, urinary retention, and osteoporosis.

In general, compounds which inhibit activation of the G-protein coupled receptor may be employed for a variety of therapeutic purposes, for example, for the treatment of hypertension, angina pectoris, myocardial infarction, ulcers, asthma, allergies, benign prostatic hypertrophy and psychotic and neurological disorders, including schizophrenia, manic excitement, depression, delirium, dementia or severe mental retardation, dyskinesias, such as Huntington's disease or Gilles dila Tourett's syndrome, among others. Compounds which inhibit G-protein coupled receptors have also been useful in reversing endogenous anorexia and in the control of bulimia.

An antibody may antagonize a G-protein coupled receptor of the present invention, or in some cases an oligopeptide, which bind to the G-protein coupled receptor but does not elicit a second messenger response such that the activity of the G-protein coupled receptors is prevented. Antibodies include anti-idiotypic antibodies which recognize unique determinants generally associated with the antigen-binding site of an antibody. Potential antagonist compounds also include proteins which are closely related to the ligand of the G-protein coupled receptors, i.e. a fragment of the ligand, which have lost biological function and when binding to the G-protein coupled receptor, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of mRNA molecules into G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

A small molecule which binds to the G-protein coupled receptor, making it inaccessible to ligands such that normal biological activity is prevented, for example small peptides or peptide-like molecules, may also be used to inhibit activation of the receptor polypeptide of the present invention.

A soluble form of the G-protein coupled receptor, e.g. a fragment of the receptors, may be used to inhibit activation of the receptor by binding to the ligand to a polypeptide of the present invention and preventing the ligand from interacting with membrane bound G-protein coupled receptors.

This invention additionally provides a method of treating an abnormal condition related to an excess of G-protein coupled receptor activity which comprises administering to a subject the inhibitor compounds as hereinabove described along with a pharmaceutically acceptable carrier in an amount effective to inhibit activation by blocking binding of ligands to the G-protein coupled receptors, or by inhibiting a second signal, and thereby alleviating the abnormal conditions.

The invention also provides a method of treating abnormal conditions related to an under-expression of G-protein coupled receptor activity which comprises administering to a subject a therapeutically effective amount of a compound which activates the receptor polypeptide of the present invention as described above in combination with a pharmaceutically acceptable carrier, to thereby alleviate the abnormal conditions.

The compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg. body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The G-protein coupled receptor polypeptides, and compounds which activate or inhibit which are also compounds may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in, viva. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pg. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining, whether the ligand binds to the G-protein coupled receptor. The systems hereinabove described for determining agonists and/or antagonists may also be employed for determining ligands which bind to the receptor.

The G-protein coupled receptor of the present invention has been putatively identified as a prostate tissue receptor. This identification has been made as a result of amino acid sequence homology.

The antagonists may be used to treat prostatic hypertrophy or prostatic cancer. The antagonists may be employed in a composition with a pharmaceutically acceptable carrier, e.g., as hereinabove described.

The agonists identified by the screening method as described above, may be employed to treat prostate cancer and prostatic hyperplasia.

When this receptor is expressed on cancer cells derived from the prostate then antibodies or small molecules that bind with high specificity to this receptor could be useful in imaging prostatic metastasis or in evaluating the completeness of a surgical resection of a tumor.

This invention further provides a method of screening drugs to identify drugs which specifically interact with, and bind to, the human G-protein coupled receptors on the surface of a cell which comprises contacting a mammalian cell comprising an isolated DNA molecule encoding the G-protein coupled receptor with a plurality of drugs, determining those drugs which bind to the mammalian cell, and thereby identifying drugs which specifically interact with and bind to a human G-protein coupled receptor of the present invention. Such drugs may then be used therapeutically to either activate or inhibit activation of the receptors of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe of the present invention capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor genes as part of a diagnostic assay for detecting diseases or susceptibility to diseases related to the presence of mutations in the nucleic acid sequences with encode the receptor polypeptides of the present invention. Such diseases, by way of example, are related to cell transformation, such as tumors and cancers.

Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the G-protein coupled receptor proteins can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Sequence differences between the reference gene and gene having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptide, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., *Human Chromosomes: a Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature,* 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy,* Alan R. Liss, Inc., pp. 77–96, 1985).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.,* 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, et al., Id., p. 146). Unless otherwise provided, ligation may be accomplished using known buffers and conditions with 10 units to T4 DNA ligase ("ligase")

per 0.5 μg of approximately equimolar amounts of the DNA fragments to be ligated.

Unless otherwise stated, transformation was performed as described in the method of Graham and Van der Eb, *Virology*, 52:456–457 (1973).

EXAMPLE 1
Expression of Recombinant HPRAJ70 in COS 7 Cells

The expression of plasmid, HPRAJ70 HA is derived from a vector pcDNAI/Amp (Invitrogen) containing: 1) GV40 origin of replication, 2) ampicillin resistance gene, 3) *E.coli* replication origin, 4) CMV promoter followed by a polylinker region, a SV40 intron and polyadenylation site. A DNA fragment encoding HPRAJT70 and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding HPRAJ70, ATCC #97,131, was constructed by PCR on the original EST cloned using two primers: the 5' primer CCCCTCCTGAATTCCAG-CAATGAGTTCCTGC (SEQ ID NO:4) contains a EcorI site followed by 12 nucleotides of coding sequence starting from the initiation codon; the 3' sequence GTG [TCTAGA] TCACTTGCCTCCCACAGCCTGCAAGTCC (SEQ ID NO:5) contains complementary sequences to XbaI site, translation stop codon, and the last 25 nucleotides of the HPRAJ70 coding sequence (not including the stop codon). Therefore, the PCR product contains a EcorI site, HPRAJ70 coding sequence, a translation termination stop codon, and an XbaI site. The PCR amplified DNA fragment and the vector, pcDNAI/Amp, were digested with EcorI and XbaI restriction enzyme and ligated. The ligation mixture was transformed into *E. coli* strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant HPRAJ70, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the HPRAJ70-HA protein was detected by radiolabelling and immunoprecipitation method. (Harlow and Lane, *Antibodies: A Laboratory Manual,* Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson et al., Id. 37:767 (1984)). Both cell lysate and culture media were precipitated with a HA specific monoclonal antibody. Proteins precipitated were analyzed on 15% SDS-PAGE gels.

EXAMPLE 2
Cloning and Expression of HPRAJ70 Using the Baculovirus Expression System The DNA sequence encoding the full length HPRAJ70 protein, ATCC #97,131, was amplified using PCR oligonucleotide primers corresponding to the 5' and 3' sequences of the gene:

The 5' primer has the sequence GTCACCCCGGGT-CAGTTCCAT<u>AT</u>GAGTTCCTGCAACTTCAC (SEQ ID NO:6) and contains a SmaI restriction enzyme site (in bold) followed by 11 nucleotides resembling an efficient signal for the initiation of translation in eukaryotic cells (Kozak, J. Mol. Biol., 196:947–950, 1987), and just behind the first 20 nucleotides of the HPRAJ70 gene (the initiation codon for translation "ATGT" is underlined).

The 3' primer has the sequence GTG TCTAGATCACTTGCCTCCCACAGCCTGCAAGTCC (SEQ ID NO:7) and contains the cleavage site for the restriction endonuclease XbaI. The amplified sequences were isolated from a 1% agarose gel by phenol extraction and ethanol ppt. The fragment was then digested with the endonucleases SmaI and XbaI and then purified as described in Example 1. This fragment is designated F2.

The vector pA2 (modification of pVL941 vector, discussed below) is used for the expression of the HPRAJ70 protein using the baculovirus expression system (for review see: Summers and Smith, *A Manual of Methods for Baculovirus Vectors and Insect Cell Culture Procedures*, Texas Agricultural Experimental Station Bulletin No. 1555, 1987). This expression vector contains the strong polyhedrin promoter of the Autographa californica nuclear polyhedrosis virus (AcMNPV) followed by the recognition sites for the restriction endonucleases SmaI and XbaI. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow and Summers, *Virology*, 170:31–39).

The plasmid was digested with the restriction enzymes SmaI and XbaI and then dephosphorylated using calf intestinal phosphatase by procedures known in the art. The DNA was then isolated from a 1% agarose gel as described in Example 1. This vector DNA is designated V2.

Fragment F2 and the dephosphorylated plasmid V2 were ligated with T4 DNA ligase. *E.coli* HB101 cells were then transformed and bacteria identified that contained the plasmid (pBac-HPRAJ70) with the HPRAJ70 gene using the enzymes SmaI and XbaI. The sequence of the cloned fragment was confirmed by DNA sequencing.

5 μg of the plasmid pBac-HPRAJ70 were co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac HPRAJ70 were mixed in a sterile well of a microtiter plate containing 50 Al of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10 fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10)

Four days after the serial dilution the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HPRAJ70 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 3
Expression Pattern of HPRAJ70 in Human Tissue

Northern blot analysis is carried out to examine the levels of expression of HPRAJ70 in human tissues. Total cellular RNA samples are isolated with RNAzol™ B system (Biotecx Laboratories, Inc. 6023 South Loop East, Houston, Tex. 77033). About 10 µg of total RNA isolated from each human tissue specified is separated on 1% agarose gel and blotted onto a nylon filter. (Sambrook et al., *Molecular Cloning-A Laboratory Manual*, Cold Spring Harbor Press, (1989)). The labeling reaction was done according to the Stratagene Prime-It kit with 50 ng DNA fragment. The labeled DNA was purified with a Select-G-50 column. (5 Prime—3 Prime, Inc. 5603 Arapahoe Road, Boulder, Colo. 80303). The filter was then hybridized with radioactive labeled full length HPRAJ70 gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for HPRAJ70 is abundant in human prostate tissue.

EXAMPLE 5
Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles-containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An antibody that specifically binds to a polypeptide having an amino acid sequence as set forth in SEQ ID NO:2.

2. The antibody of claim 1, which is a monoclonal antibody.

3. The antibody of claim 1, which is a polyclonal antibody.

4. The antibody of claim 1, which is a chimeric antibody.

5. The antibody of claim 1, which is a humanized antibody.

6. The antibody of claim 1, which is a human antibody.

7. A pharmaceutical composition comprising the antibody of claim 1 and a pharmaceutically acceptable carrier.

8. The pharmaceutical composition of claim 7, wherein the antibody is a monoclonal antibody.

9. The pharmaceutical composition of claim 7, wherein the antibody is a humanized monoclonal antibody.

10. The pharmaceutical composition of claim 7, wherein the antibody is a human monoclonal antibody.

11. A single chain antibody that specifically binds to a polypeptide having an amino acid sequence as set forth in SEQ ID NO:2.

12. A pharmaceutical composition comprising the single chain antibody of claim 11 and a pharmaceutically acceptable carrier.

13. A Fab fragment that specifically binds to a polypeptide having an amino acid sequence as set forth in SEQ ID NO:2.

14. A pharmaceutical composition comprising the Fab fragment of claim 13 and a pharmaceutically acceptable carrier.

15. A hybridoma cell line that produces a monoclonal antibody that binds to a polypeptide having an amino acid sequence as set forth in SEQ ID NO:2.

16. An antibody produced by immunizing an animal with a polypeptide having an amino acid sequence as set forth in SEQ ID NO:2, which antibody specifically binds to said polypeptide.

17. An antibody that specifically binds to the mature polypeptide encoded by the cDNA contained in ATCC Deposit No. 97131.

18. The antibody of claim 17, which is a monoclonal antibody.

19. The antibody of claim 17, which is a polyclonal antibody.

20. The antibody of claim 17, which is a chimeric antibody.

21. The antibody of claim 17, which is a humanized antibody.

22. The antibody of claim 17, which is a human antibody.

23. A pharmaceutical composition comprising the antibody of claim 17, and a pharmaceutically acceptable carrier.

24. The pharmaceutical composition of claim 23, wherein the antibody is a monoclonal antibody.

25. The pharmaceutical composition of claim 23, wherein the antibody is a humanized monoclonal antibody.

26. The pharmaceutical composition of claim 23, wherein the antibody is a human monoclonal antibody.

27. A single chain antibody that specifically binds to the mature polypeptide encoded by the cDNA contained in ATCC Deposit No. 97131.

28. A pharmaceutical composition comprising the single chain antibody of claim 27 and a pharmaceutically acceptable carrier.

29. An Fab fragment that specifically binds to the mature polypeptide encoded by the cDNA contained in ATCC Deposit No. 97131.

30. A pharmaceutical composition comprising the Fab fragment of claim 29 and a pharmaceutically acceptable carrier.

31. A hybridoma cell line that produces a monoclonal antibody that binds to the mature polypeptide encoded by the cDNA contained in ATCC Deposit No. 97131.

32. An antibody produced by immunizing an animal with the polypeptide encoded by the cDNA contained in ATCC Deposit No 97131, which antibody specifically binds to said polypeptide.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
    (A) LENGTH: 1474 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 274..1233

(xi) SEQUENCE DESCRIPTION: SEQ ID NO:1:

```
CCATGCTGCC TTCCGGGCAG TACCATCCAT CTCCACACCC TGGAAGACAC A GTGAGTTAG      60

CACCACCACC AGGTAATTGG CCTTATCAGC TCTGTGCCTG TCTCCAGTCA G GCTGGAATA     120

AGTCTCCTCA TATGTGCAAG CTCGGCCCTC CCCTGGAATC TAAAGCCTCC T CAGCCTTCT     180

GAGTCAGCCT GAAAGGAACA GGCCGAACTG CTGTATGGGC TCTACTGCCA G TGTGACCTC     240

ACCCTCTCCA GTCACCCCTC CTCAGTTCCA GCT ATG AGT TCC T GC AAC TTC ACA      294
                                   Met Ser Ser Cys Asn Phe Thr
                                    1               5

CAT GCC ACC TGT GTG CTT ATT GGT ATC CCA G GA TTA GAG AAA GCC CAT       342
His Ala Thr Cys Val Leu Ile Gly Ile Pro G ly Leu Glu Lys Ala His
             10                  15                 20

TTC TGG GTT GGC TTC CCC CTC CTT TCC ATG T AT GTA GTG GCA ATG TGT       390
Phe Trp Val Gly Phe Pro Leu Leu Ser Met T yr Val Val Ala Met Cys
 25                  30                  35

GGA AAC TGC ATC GTG GTC TTC ATC GTA AGG A CG GAA CGC AGC CTG CAC       438
Gly Asn Cys Ile Val Val Phe Ile Val Arg T hr Glu Arg Ser Leu His
 40                  45                  50                  55

GCT CCG ATG TAC CTC TTT CTC TGC ATG CTT G CA GCC ATT GAC CTG GCC       486
Ala Pro Met Tyr Leu Phe Leu Cys Met Leu A la Ala Ile Asp Leu Ala
             60                  65                  70

TTA TCC ACA TCC ACC ATG CCT AAG ATC CTT G CC CTT TTC TGG TTT GAT       534
Leu Ser Thr Ser Thr Met Pro Lys Ile Leu A la Leu Phe Trp Phe Asp
             75                  80                  85

TCC CGA GAG ATT AGC ATT GAG GCC TGT CTT A CC CAG ATG TTC TTT ATT       582
Ser Arg Glu Ile Ser Ile Glu Ala Cys Leu T hr Gln Met Phe Phe Ile
         90                  95                 100

CAT GCC CTC TCA GCC ATT GAA TCC ACC ATC C TG CTG GCC ATG GCC TTT       630
His Ala Leu Ser Ala Ile Glu Ser Thr Ile L eu Leu Ala Met Ala Phe
        105                 110                 115

GAC CGT TAT GTG GCC ATC TGC CAC CCA CTG C GC CAT GCT GCA GTG CTC       678
Asp Arg Tyr Val Ala Ile Cys His Pro Leu A rg His Ala Ala Val Leu
120                 125                 130                 135

AAC AAT ACA GTA ACA GCC CAG ATT GGC ATC G TG GCT GTG GTC CGC GGA       726
Asn Asn Thr Val Thr Ala Gln Ile Gly Ile V al Ala Val Val Arg Gly
                140                 145                 150

TCC CTC TTT TTT TTC CCA CTG CCT CTG CTG A TC AAG CGG CTG GCC TTC       774
Ser Leu Phe Phe Phe Pro Leu Pro Leu Leu I le Lys Arg Leu Ala Phe
            155                 160                 165

TGC CAC TCC AAT GTC CTC TCG CAC TCC TAT T GT GTC CAC CAG GAT GTA       822
Cys His Ser Asn Val Leu Ser His Ser Tyr C ys Val His Gln Asp Val
            170                 175                 180

ATG AAG TTG GCC TAT GCA GAC ACT TTG CCC A AT GTG GTA TAT GGT CTT       870
Met Lys Leu Ala Tyr Ala Asp Thr Leu Pro A sn Val Val Tyr Gly Leu
            185                 190                 195

ACT GCC ATT CTG CTG GTC ATG GGC GTG GAC G TA ATG TTC ATC TCC TTG       918
Thr Ala Ile Leu Leu Val Met Gly Val Asp V al Met Phe Ile Ser Leu
200                 205                 210                 215

TCC TAT TTT CTG ATA ATA CGA ACG GTT CTG C AA CTG CCT TCC AAG TCA       966
```

```
Ser Tyr Phe Leu Ile Ile Arg Thr Val Leu G ln Leu Pro Ser Lys Ser
            220                 225                 230

GAG CGG GCC AAG GCC TTT GGA ACC TGT GTG T CA CAC ATT GGT GTG GTA    1014
Glu Arg Ala Lys Ala Phe Gly Thr Cys Val S er His Ile Gly Val Val
            235                 240                 245

CTC GCC TTC TAT GTG CCA CTT ATT GGC CTC T CA GTT GTA CAC CGC TTT    1062
Leu Ala Phe Tyr Val Pro Leu Ile Gly Leu S er Val Val His Arg Phe
            250                 255                 260

GGA AAC AGC CTT CAT CCC ATT GTG CGT GTT G TC ATG GGT GAC ATC TAC    1110
Gly Asn Ser Leu His Pro Ile Val Arg Val V al Met Gly Asp Ile Tyr
            265                 270                 275

CTG CTG CTG CCT CCT GTC ATC AAT CCC ATC A TC TAT GGT GCC AAA ACC    1158
Leu Leu Leu Pro Pro Val Ile Asn Pro Ile I le Tyr Gly Ala Lys Thr
280                 285                 290                 295

AAA CAG ATC AGA ACA CGG GTG CTG GCT ATG T TC AAG ATC AGC TGT GAC    1206
Lys Gln Ile Arg Thr Arg Val Leu Ala Met P he Lys Ile Ser Cys Asp
            300                 305                 310

AAG GAC TTG CAG GCT GTG GGA GGC AAG TGACCCTT AA CACTACACTT          1253
Lys Asp Leu Gln Ala Val Gly Gly Lys
            315                 320

CTCCTTATCT TTATTGGCTT GATAAACATA ATTATTTCTA ACACTAGCTT A TTTCCAGTT    1313

GCCCATAAGC ACATCAGTAC TTTTCTCTGG CTGGAATAGT AAACTAAAGT A TGGTACATC    1373

TACCTAAAGG ACTATTATGT GGAATAATAC ATACTAATGA AGTATTACAT G ATTTAAAGA    1433

CTACAATAAA ACCAAACATG CTTATAACAT TAAAAAAAAA A                       1474

(2) INFORMATION FOR SEQ ID NO:2:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Cys Asn Phe Thr His Ala Thr C ys Val Leu Ile Gly Ile
  1               5                  10                  15

Pro Gly Leu Glu Lys Ala His Phe Trp Val G ly Phe Pro Leu Leu Ser
             20                  25                  30

Met Tyr Val Val Ala Met Cys Gly Asn Cys I le Val Val Phe Ile Val
             35                  40                  45

Arg Thr Glu Arg Ser Leu His Ala Pro Met T yr Leu Phe Leu Cys Met
         50                  55                  60

Leu Ala Ala Ile Asp Leu Ala Leu Ser Thr S er Thr Met Pro Lys Ile
 65                  70                  75                  80

Leu Ala Leu Phe Trp Phe Asp Ser Arg Glu I le Ser Ile Glu Ala Cys
             85                  90                  95

Leu Thr Gln Met Phe Phe Ile His Ala Leu S er Ala Ile Glu Ser Thr
             100                 105                 110

Ile Leu Leu Ala Met Ala Phe Asp Arg Tyr V al Ala Ile Cys His Pro
         115                 120                 125

Leu Arg His Ala Ala Val Leu Asn Asn Thr V al Thr Ala Gln Ile Gly
         130                 135                 140

Ile Val Ala Val Val Arg Gly Ser Leu Phe P he Phe Pro Leu Pro Leu
145                 150                 155                 160

Leu Ile Lys Arg Leu Ala Phe Cys His Ser A sn Val Leu Ser His Ser
             165                 170                 175
```

```
Tyr Cys Val His Gln Asp Val Met Lys Leu Ala Tyr Ala Asp Thr Leu
            180                 185                 190

Pro Asn Val Val Tyr Gly Leu Thr Ala Ile Leu Leu Val Met Gly Val
            195                 200                 205

Asp Val Met Phe Ile Ser Leu Ser Tyr Phe Leu Ile Ile Arg Thr Val
            210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
            245                 250                 255

Leu Ser Val Val His Arg Phe Gly Asn Ser Leu His Pro Ile Val Arg
            260                 265                 270

Val Val Met Gly Asp Ile Tyr Leu Leu Leu Pro Pro Val Ile Asn Pro
            275                 280                 285

Ile Ile Tyr Gly Ala Lys Thr Lys Gln Ile Arg Thr Arg Val Leu Ala
            290                 295                 300

Met Phe Lys Ile Ser Cys Asp Lys Asp Leu Gln Ala Val Gly Gly Lys
305                 310                 315                 320

(2) INFORMATION FOR SEQ ID NO:3:

(i) SEQUENCE CHARACTERISTICS:
        (A) LENGTH: 247 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Phe Leu Leu Leu Gly Leu Pro Ile Gln Pro Glu Gln Gln Asn Leu Cys
1               5                   10                  15

Tyr Ala Leu Phe Leu Ala Met Tyr Leu Thr Thr Leu Leu Gly Asn Leu
            20                  25                  30

Leu Ile Ile Val Leu Ile Arg Leu Asp Ser His Leu His Thr Pro Met
            35                  40                  45

Tyr Leu Phe Leu Ser Asn Leu Ser Phe Ser Asp Leu Cys Phe Ser Ser
            50                  55                  60

Val Thr Ile Pro Lys Leu Leu Gln Asn Met Gln Asn Gln Asp Pro Ser
65                  70                  75                  80

Ile Pro Tyr Ala Asp Cys Leu Thr Gln Met Tyr Phe Phe Leu Leu Phe
                85                  90                  95

Gly Asp Leu Glu Ser Phe Leu Leu Val Ala Met Ala Tyr Asp Arg Tyr
            100                 105                 110

Val Ala Ile Cys Phe Pro Leu His Tyr Thr Ala Ile Met Ser Pro Met
            115                 120                 125

Leu Cys Leu Ala Leu Val Ala Leu Ser Trp Val Leu Thr Thr Phe His
            130                 135                 140

Ala Met Leu His Thr Leu Leu Met Ala Arg Leu Cys Phe Cys Ala Asp
145                 150                 155                 160

Asn Val Ile Pro His Phe Phe Cys Asp Met Ser Ala Leu Leu Lys Leu
                165                 170                 175

Ala Phe Ser Asp Thr Arg Val Asn Glu Trp Val Ile Phe Ile Met Gly
            180                 185                 190

Gly Leu Ile Leu Val Ile Pro Phe Leu Leu Ile Leu Gly Ser Tyr Ala
            195                 200                 205
```

```
Arg Ile Val Ser Ser Ile Leu Lys Val Pro S er Ser Lys Gly Ile Cys
    210                 215                 220

Lys Ala Phe Ser Thr Cys Gly Ser His Leu S er Val Val Ser Leu Phe
225                 230                 235                 240

Tyr Gly Thr Val Ile Gly Leu
                245
```

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:4:

```
CCCCTCCTGA ATTCCAGCAA TGAGTTCCTG C                              31
```

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:5:

```
GTGTCTAGAT CACTTGCCTC CCACAGCCTG CAAGTCC                        37
```

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:6:

```
GTCACCCCGG GTCAGTTCCA TCATGAGTTC CTGCAACTTC AC                  42
```

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:7:

```
GTGTCTAGAT CACTTGCCTC CCACAGCCTG CAAGTCC                        37
```

(2) INFORMATION FOR SEQ ID NO:8:

(i) SEQUENCE CHARACTERISTICS:
        (A) LENGTH: 26 amino acids

```
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Val Met Ala Met Met Tyr Thr Val Val Thr P ro Met Leu Asn Pro Phe
1               5                   10                  15

Ile Tyr Ser Leu Arg Asn Arg Asp Met Lys
            20                  25
```